(12) United States Patent
Fujiwara et al.

(10) Patent No.: US 7,785,271 B2
(45) Date of Patent: Aug. 31, 2010

(54) SENSOR FOR BLOOD COMPONENT ANALYSIS

(75) Inventors: Masaki Fujiwara, Matsuyama (JP); Shin Ikeda, Katano (JP)

(73) Assignee: Panasonic Corporation, Osaka (JP)

( * ) Notice: Subject to any disclaimer, the term of this patent is extended or adjusted under 35 U.S.C. 154(b) by 1068 days.

(21) Appl. No.: 10/952,702

(22) Filed: Sep. 28, 2004

(65) Prior Publication Data
US 2005/0123443 A1 Jun. 9, 2005

(30) Foreign Application Priority Data
Oct. 2, 2003 (JP) ............................. 2003-344762

(51) Int. Cl.
*A61B 5/00* (2006.01)
(52) U.S. Cl. ...................................................... 600/583
(58) Field of Classification Search ................. 600/583, 600/300, 301; 604/19, 103.01, 406, 403; 204/409, 403.11; 606/194
See application file for complete search history.

(56) References Cited

U.S. PATENT DOCUMENTS

| 6,129,823 | A * | 10/2000 | Hughes et al. | ............ | 204/403.1 |
| 2003/0186228 | A1 * | 10/2003 | McDevitt et al. | ................ | 435/6 |
| 2004/0182703 | A1 * | 9/2004 | Bell et al. | ............... | 204/403.11 |
| 2006/0064035 | A1 * | 3/2006 | Wang et al. | .................. | 600/583 |

FOREIGN PATENT DOCUMENTS

JP 2001-346781 A 12/2001

* cited by examiner

*Primary Examiner*—Max Hindenburg
*Assistant Examiner*—Fangemonique Smith
(74) *Attorney, Agent, or Firm*—Hamre, Schumann, Mueller & Larson, P.C.

(57) ABSTRACT

A sensor for blood component analysis, which allows even a trace amount of blood to be led to an analysis portion reliably. The sensor for blood component analysis includes a substrate, a spacer, and a cover. The cover is disposed on the substrate with the spacer intervening between the cover and the substrate, whereby a space that serves as an analysis portion and a channel for leading blood to the analysis portion is formed inside the sensor. Through holes are formed in the substrate and the spacer, respectively, so that a common through hole through which a needle of a lancet can pass is formed when the spacer is disposed on the substrate. The through hole of the spacer communicates with the channel and a top of the through hole of the spacer is covered with the cover, whereby a lancing portion is formed by the common through hole and a portion of the cover covering the top of the through hole of the spacer. In use, the sensor is placed at a position where blood collection is to be performed, the portion of the cover covering the lancing portion is broken through with the needle of the lancet so that the needle is allowed to pass through the common through hole to puncture the position, and blood that has come out is guided by a downwardly protruding burr formed when the cover is broken through so that the blood is led to the channel and flows through the channel to be led to the analysis portion.

9 Claims, 5 Drawing Sheets

SENSOR FOR BLOOD COMPONENT ANALYSIS

BACKGROUND OF THE INVENTION

1. Field of the Invention

The present invention relates to a sensor for blood component analysis.

2. Related Background Art

Conventionally, sensors for blood component analysis have been used for clinical test, self-measurement of blood glucose level by diabetics, etc. (see JP 2001-346781 A, for example). FIG. 10 shows an example of a sensor for measuring a blood glucose level. As shown in FIG. 10, in this sensor 1000, a working electrode 1002 and a counter electrode 1003 are formed on an insulating base material 1001, and a reagent layer is disposed on these electrodes, thereby forming an analysis portion 1004. The reagent layer contains an oxidoreductase (e.g., glucose oxidase), a mediator, and the like. A cover 1005 is disposed on the substrate 1001 so as to cover an entire area excluding one end portion (the end portion on the right in FIG. 10) with a spacer (not shown) intervening therebetween. The analysis portion 1004 communicates with a channel 1018 for leading blood to the analysis portion. The channel 1018 extends to the other end portion (the end portion on the left in FIG. 10) of the sensor, and the tip of the channel 1018 is open toward the outside of the sensor so as to serve as a blood inlet port 1019. The working electrode 1002 is connected to a lead 1022, and the counter electrode 1003 is connected to a lead 1023. These leads extend to the above-described one end portion of the sensor with the tip of each lead not being covered with the cover but being exposed.

Measurement of blood glucose level using this sensor can be carried out in the following manner, for example. First, a fingertip or the like is punctured with a dedicated lancet to cause bleeding. On the other hand, the sensor is set in a dedicated measuring device. The blood inlet port of the sensor that is set in the measuring device is brought into contact with the blood that has come out, so that the blood is led to the analysis portion in the sensor by a capillary phenomenon. In the analysis portion, glucose in the blood reacts with the oxidoreductase such as glucose oxidase contained in the reagent. Thus, when a voltage is applied between the electrodes after a lapse of a certain period, a redox current flows. The electrodes detect the current, which is then measured by the measuring device. The measuring device converts the measured value into an amount of glucose and displays the value obtained by the conversion.

In recent years, in the development of sensors for blood component analysis to be used for self-measurement, various efforts have been made to reduce the amount of blood required for the measurement, as one attempt to alleviate the burden on the subjects. However, as the amount of blood is reduced, it becomes more difficult to supply the blood to an analysis portion of a sensor, which may result in failure of measurement or measurement errors.

SUMMARY OF THE INVENTION

With the foregoing in mind, it is an object of the present invention to provide a sensor for blood component analysis capable of achieving reliable measurement using a trace amount of blood.

In order to achieve the above object, a sensor for blood component analysis according to the present invention includes: a substrate, a spacer, and a cover. The cover is disposed on the substrate with the spacer intervening between the cover and the substrate, whereby a space that serves as an analysis portion and a channel for leading blood to the analysis portion is formed inside the sensor. Through holes are formed in the substrate and the spacer, respectively, so that a common through hole through which a needle or an edge of a lancet can pass is formed when the spacer is disposed on the substrate. The through hole of the spacer communicates with the channel and a top of the through hole of the spacer is covered with the cover, whereby a lancing portion is formed by the common through hole and a portion of the cover covering the top of the through hole of the spacer. In use, the sensor is placed at a position where blood collection is to be performed, the portion of the cover covering the lancing portion is broken through with the needle or the edge of the lancet so that the needle or the edge is allowed to pass through the common through hole to puncture the position, and blood that has come out is guided by a downwardly protruding burr formed when the cover is broken through so that the blood is led to the channel and flows through the channel to be led to the analysis portion.

In the sensor of the present invention, when the cover is broken through with the needle or the edge of the lancet, the burr protruding downward is formed in the lancing portion of the cover. The blood that has come out from the position where the blood collection is performed is guided by this burr so that it is led from the through hole to the channel due to its surface tension and flows through the channel to be led to the analysis portion. Since the blood is guided by the burr so that it is led from the through hole to the channel, even a trace amount of blood can be led to the analysis portion reliably. Thus, it is possible to make a wound created by the sensor small, which allows the subject to carry out less painful measurement, for example.

Moreover, in the self-measurement of blood glucose level by diabetics, delicate operations of lancing and collecting blood have been a significant burden on diabetics whose eyesight generally is not very good. However, according to the sensor of the present invention, lancing and blood collection can be performed at the same time. Thus, the sensor of the present invention also is advantageous in that even a person with poor eyesight, e.g., a diabetic, can use the sensor easily.

DETAILED DESCRIPTION OF THE INVENTION

In the present invention, it is preferable that a plurality of channels and analysis portions are provided with respect to one lancing portion. With this configuration, a plurality of items can be measured by performing lancing only once.

In the present invention, it is preferable that a plurality of lancing portions are provided in one sensor, and at least one channel and analysis portion are provided with respect to each lancing portion. With this configuration, one sensor can be used in a plurality of measurements.

In the present invention, it is preferable that at least the lancing portion of the cover is hydrophilic. Blood normally is hydrophilic. Thus, when the lancing portion of the cover is hydrophilic, blood can adhere well to the burr formed. Accordingly, with this configuration, blood can be supplied to the analysis portion more reliably.

In the present invention, it is preferable that an air vent hole is provided in a portion of the cover that corresponds to the channel. By providing the air vent hole, it is possible to cause a capillary phenomenon.

The sensor of the present invention may be, for example, a sensor utilizing a redox reaction. In this case, a reagent containing an oxidoreductase that reacts with an analyte is disposed on the analysis portion, and the amount of the analyte is measured by causing a redox reaction between the oxidoreductase and the analyte contained in the blood and then measuring the degree to which the redox reaction has occurred. The degree to which the redox reaction has occurred can be measured by optical means or electrochemical means, for example. The measurement using the optical means can be achieved by forming the reagent layer so as to contain a substrate that develops color by the redox reaction in addition to the oxidoreductase and measuring the degree of the color developed by this substrate with an optical measuring device such as a spectrophotometer. On the other hand, the measurement using the electrochemical means can be achieved by disposing the electrodes in the analysis portion and measuring a current generated by the redox reaction with these electrodes. In this case, the reagent preferably contains a mediator.

An analyte to which the sensor of the present invention is applicable is not particularly limited, and examples thereof include glucose, lactic acid, and cholesterol in blood. The oxidoreductase to be contained in the reagent may be selected depending on the analyte. For example, when the analyte is glucose in blood, the oxidoreductase may be glucose oxidase or glucose dehydrogenase.

Hereinafter, an example of a sensor according to the present invention will be described with reference to the drawings.

Figure 1:
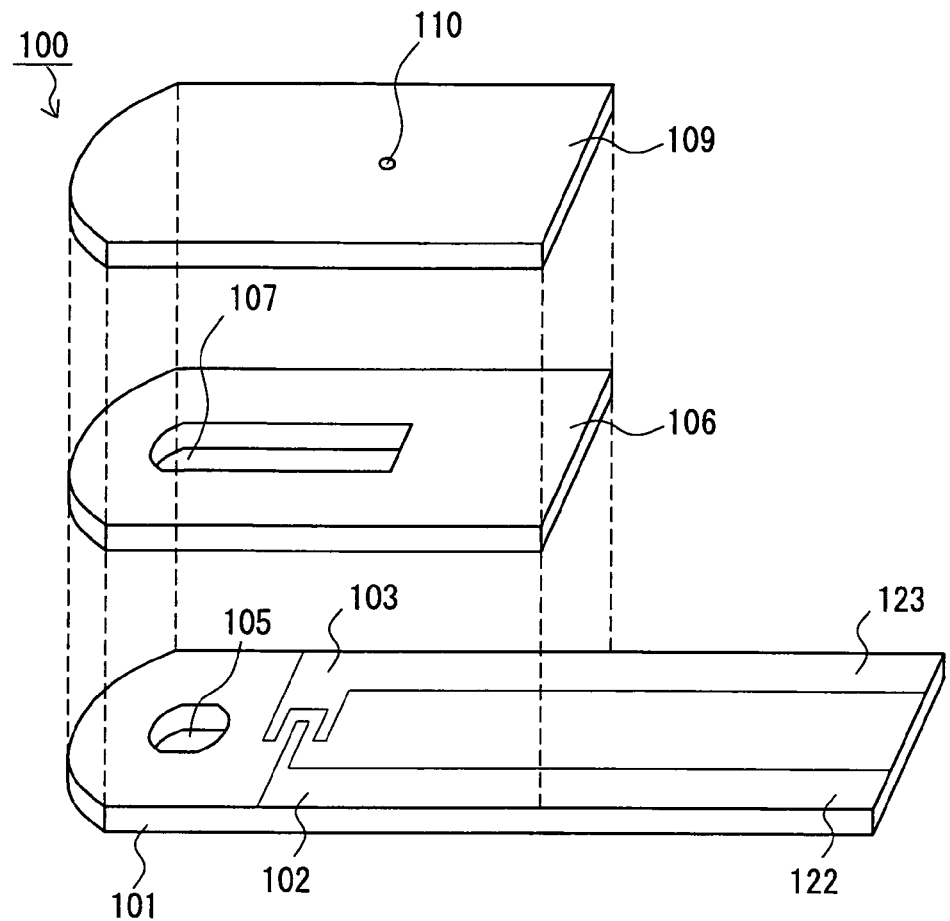
FIG. 1 is an exploded perspective view showing an example of a sensor for blood component analysis according to the present invention.
Figure 2:
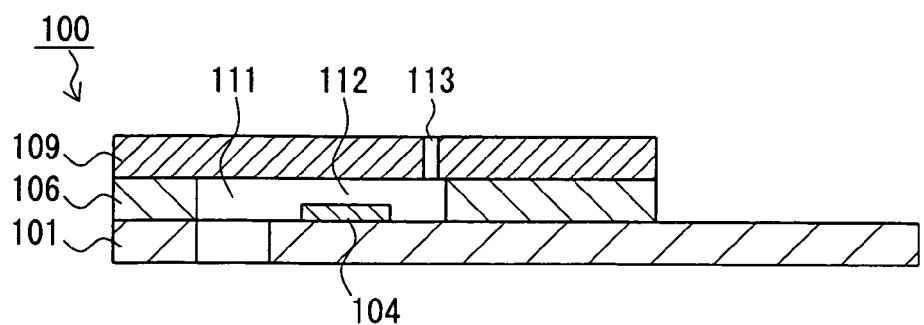
FIG. 2 is a side view of the sensor shown in FIG. 1.

FIG. 1 and FIG. 2 shows an example of a sensor according to the present invention. Note here that the sensor shown in FIG. 1 and FIG. 2 is a sensor with a basic structure. FIG. 1 is an exploded view of the sensor, and FIG. 2 is a cross-sectional view of the same.

As shown in the drawings, in this sensor 100, a cover 109 is disposed on an insulating substrate 101 with a spacer 106 intervening therebetween. On the insulating substrate 101, a working electrode 102 and a counter electrode 103 are formed, which are connected to a lead 122 and a lead 123, respectively. Furthermore, the insulating substrate 101 has a through hole 105 through which a needle or an edge of a lancet can pass. The spacer 106 has a space 107 that serves as a through hole through which a needle or an edge of a lancet can pass and also as a channel. The cover 109 has an air vent hole 110 at a portion corresponding to the rear side of the channel. The through hole 105 of the insulating substrate 101 and a part of the space 107 of the spacer 106 together form a through hole through which a needle or an edge of a lancet can pass. The top of this through hole is covered with the cover, thereby forming a lancing portion. The remaining portion of the space 107 of the spacer 106 serves as a channel 112. Furthermore, as shown in FIG. 2, a reagent layer 104 is disposed on the working electrode 102 and the counter electrode 103, thereby forming an analysis portion.

In the present invention, the material for the insulating substrate is not particularly limited, and may be, for example, polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), polymethyl methacrylate (PMMA), an ABS resin (ABS), or glass. Among them, polyethylene terephthalate (PET), polycarbonate (PC), and polyimide (PI) are preferable, and polyethylene terephthalate (PET) is more preferable. The size of the insulating substrate is not particularly limited. For example, the insulating substrate may have an overall length of 5 mm to 100 mm, a width of 3 mm to 50 mm, and a thickness of 0.1 mm to 2 mm; preferably an overall length of 10 mm to 50 mm, a width of 3 mm to 20 mm, and a thickness of 0.2 mm to 1 mm; and more preferably an overall length of 15 mm to 30 mm, a width of 5 mm to 10 mm, and a thickness of 0.3 mm to 0.6 mm. In the insulating substrate, the through hole may be formed, for instance, by perforating the insulating substrate with a laser, a drill, or the like, or by forming the insulating substrate using a die that can form the insulating substrate provided with the through hole. The shape of the through hole is not particularly limited, and may be circular, oval, semicircular, semioval, polygonal, or the like. The maximum diameter of the through hole is not particularly limited, and may be, for example, 0.5 mm to 20 mm, preferably 0.5 mm to 5 mm, and more preferably 1 mm to 3 mm.

The electrodes and leads on the insulating substrate may be formed, for example, by forming a conductive layer with gold, platinum, palladium, or the like by sputtering or vapor deposition and then processing the conductive layer into a particular electrode pattern with a laser. Examples of the laser include YAG lasers, $CO_2$ lasers, and excimer lasers.

The reagent layer contains an oxidoreductase, a mediator, and the like, for example. When an analyte is glucose in blood, the oxidoreductase may be glucose oxidase, glucose dehydrogenase, or the like. Examples of the mediator include potassium ferricyanide. In addition to the oxidoreductase and the mediator, the reagent layer further may contain a hydrophilic polymer, an enzyme stabilizer, a crystal homogenizing agent, and the like, for example. The hydrophilic polymer serves to keep the reagent layer in a predetermined shape (i.e., the hydrophilic polymer serves as an excipient), and examples thereof include carboxymethyl cellulose (CMC). The enzyme stabilizer prevents an enzyme from being deteriorated during storage, and examples thereof include maltitol. The crystal homogenizing agent serves to homogenize the reagent layer, which allows the reagent layer to dissolve quickly and uniformly when blood touches it. Examples of the crystal homogenizing agent include taurine.

The reagent layer can be formed, for example, by dissolving a predetermined reagent in water or a buffer solution and then drying it. As one example, the reagent layer can be formed in the following manner. First, in a 0.01 wt % to 2.0 wt % CMC aqueous solution, 0.1 U/sensor to 5.5 U/sensor of PQQ-GDH, 10 mM to 200 mM of potassium ferricyanide, 0.05 mM to 30 mM of maltitol, and 10 mM to 300 mM of taurine are added and dissolved. The reagent layer can be formed by dropping the thus-obtained solution on the analysis portion of the substrate and then drying it. The drying may be either air drying or forced drying using warm air. However, if the temperature of the warm air is too high, there is a possibility that the enzyme contained in the solution might be deactivated. Thus, the temperature of the warm air preferably is around 50° C.

In the present invention, the material for the spacer is not particularly limited. For example, the same material as that for the insulating substrate can be used. The size of the spacer also is not particularly limited. For example, the spacer may have an overall length of 5 mm to 100 mm, a width of 3 mm to 50 mm, and a thickness of 0.01 mm to 1 mm; preferably an overall length of 10 mm to 50 mm, a width of 3 mm to 20 mm, and a thickness 0.05 mm to 0.5 mm; and more preferably an overall length of 15 mm to 30 mm, a width of 5 mm to 10 mm, and a thickness of 0.05 mm to 0.25 mm. The spacer has the space that serves as the through hole and as the channel This space may have, for example, an overall length of 1 mm to 30 mm and a width of 0.05 mm to 10 mm, preferably an overall length of 2 mm to 10 mm and a width of 0.3 mm to 5 mm, and more preferably an overall length of 2 mm to 10 mm and a width of 0.5 mm to 2 mm. This space can be formed in the same manner as the through hole of the insulating substrate.

In the present invention, the material for the cover is not particularly limited. For example, the same material as that for the insulating substrate can be used. It is more preferable that not only a portion of the cover corresponding to the lancing portion but also a portion of the cover corresponding to the ceiling of the sample supply channel is subject to a treatment for imparting hydrophilicity. The treatment for imparting hydrophilicity may be carried out by, for example, applying a detergent or introducing a hydrophillic functional group such as a hydroxyl group, a carbonyl group, or a carboxyl group to the cover surface by plasma processing or the like. The size of the cover is not particularly limited. For example, the cover may have an overall length of 5 mm to 100 mm, a width of 3 mm to 50 mm, and a thickness of 0.01 mm to 0.5 mm; preferably an overall length of 10 mm to 50 mm, a width of 3 mm to 20 mm, and a thickness of 0.05 mm to 0.25 mm; and more preferably an overall length of 15 mm to 30 mm, a width of 5 mm to 10 mm, and a thickness of 0.05 mm to 0.1 mm. The cover preferably has an air vent hole, which may have, for example, a maximum diameter of 0.01 mm to 10 mm, preferably 0.05 mm to 5 mm, and more preferably 0.1 mm to 2 mm. The air vent hole can be formed in the same manner as the through hole of the insulating substrate.

The sensor of the present invention can be produced by laminating the insulating substrate, the spacer, and the cover in this order and integrating them. The integration can be achieved by adhering these three components with an adhesive or through heat-sealing. As the adhesive, an epoxy adhesive, an acrylic adhesive, a polyurethane adhesive, a thermosetting adhesive (a hot melt adhesive or the like), a UV curable adhesive, or the like can be used, for example.

Figure 3:
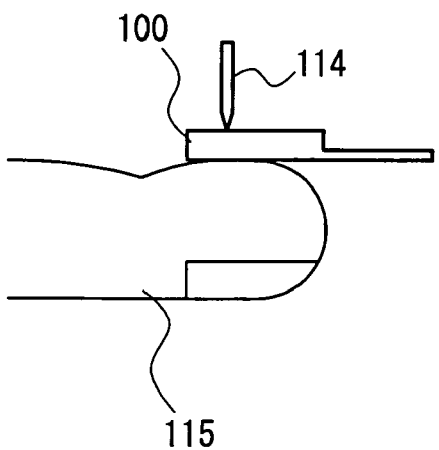
FIG. 3 is a cross-sectional view showing an example of a method of using the sensor.
Figure 4:
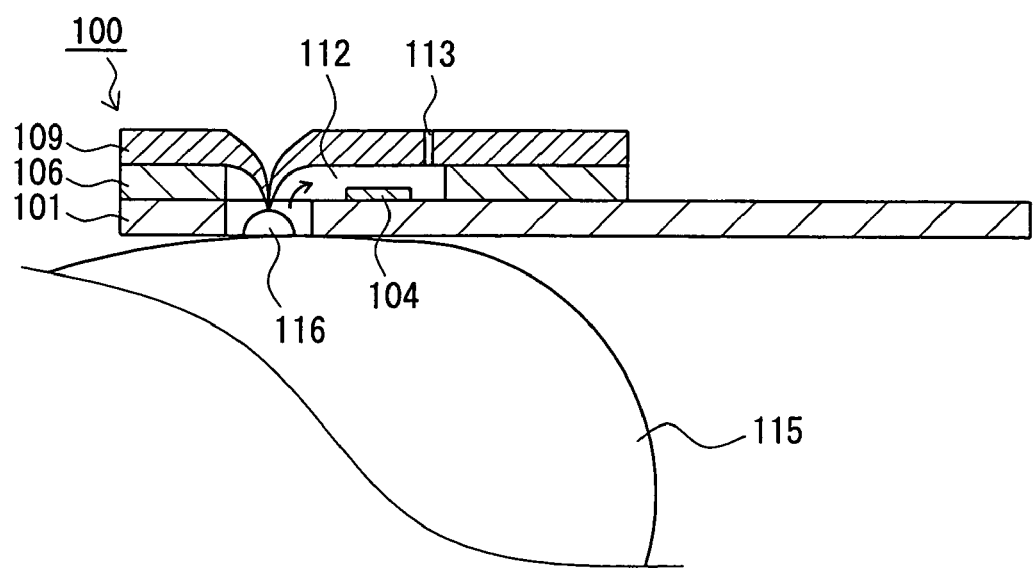
FIG. 4 is a cross-sectional view showing another example of a method of using the sensor.

Next, the method of using the sensor shown in FIG. 1 and FIG. 2 will be described. First, the sensor is set in a predetermined dedicated measuring device. In this state, the sensor 100 is placed on a pulp of a finger 115, as shown in FIG. 3. Then, the pulp of the finger 115 is punctured with a needle 114 of a lancet. By so doing, as shown in FIG. 4, the needle breaks through a lancing portion of the cover 109, passes through a through hole, and then injures the pulp of the finger 115 to cause bleeding. At this time, a burr protruding downward is formed in the lancing portion of the cover 109. Blood 116 coming out from the finger 115 is guided by the burr so that, as indicated by the arrow, it flows through the channel 112 to be led to an analysis portion, where the blood 116 comes into contact with the reagent layer 104 to cause a component in the blood 116 to react with an oxidoreductase or the like contained in the reagent layer 104. When a voltage is applied between the electrodes after a lapse of a certain period, a redox current flows due to the redox reaction caused by the oxidoreductase. The redox current is detected by the working electrode and the counter electrode, which then is measured by the dedicated measuring device. The measuring device converts the measured value into an amount of the blood component and displays the value obtained by the conversion. Note here that in FIG. 4 the same reference numerals are assigned to the same elements as in FIG. 1 and FIG. 2. In the above-described example of a method of using the sensor, lancing is performed with the sensor being set in the measuring device. However, the present invention is not limited thereto. For example, lancing may be performed without setting the sensor in the measuring device and the sensor may be set in the measuring device after the lancing.

Figure 5:
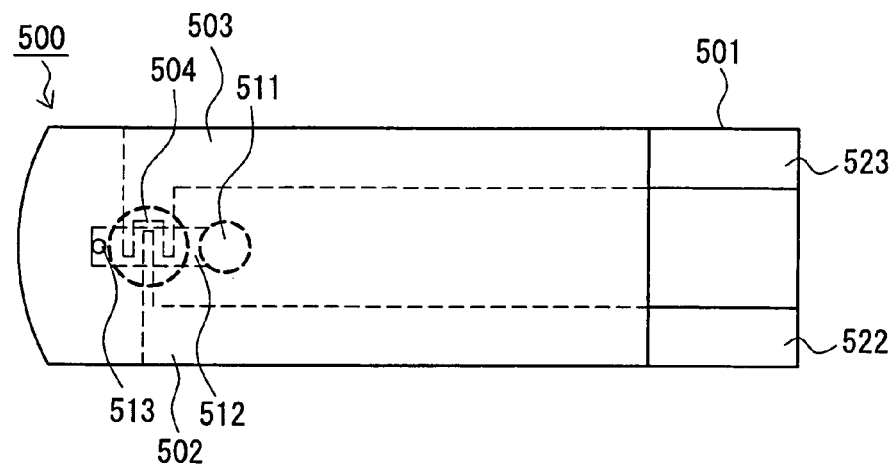
FIG. 5 is a plan view showing another example of a sensor for blood component analysis according to the present invention.

Next, another example of the sensor of the present invention is shown in FIG. 5. In this sensor 500, the positional relationship between an analysis portion and a lancing portion is inverse to that in the above-described sensor (see FIG. 1 and FIG. 2). More specifically, in this sensor, a lancing portion 511 is located closer to one end with respect to the center of the sensor (on the left in FIG. 5), and an analysis portion is located still closer to the end. Except for the above, the sensor 500 is configured in the same manner as the above sensor, and the size, materials, production method, method of use, etc. also are the same as those of the above sensor. In FIG. 5, reference numeral 501 denotes an insulating substrate, 502 denotes a working electrode, 503 denotes a counter electrode, 522 and 523 denote a lead, 504 denotes a reagent layer, and 513 denotes an air vent hole of a cover.

Figure 6:
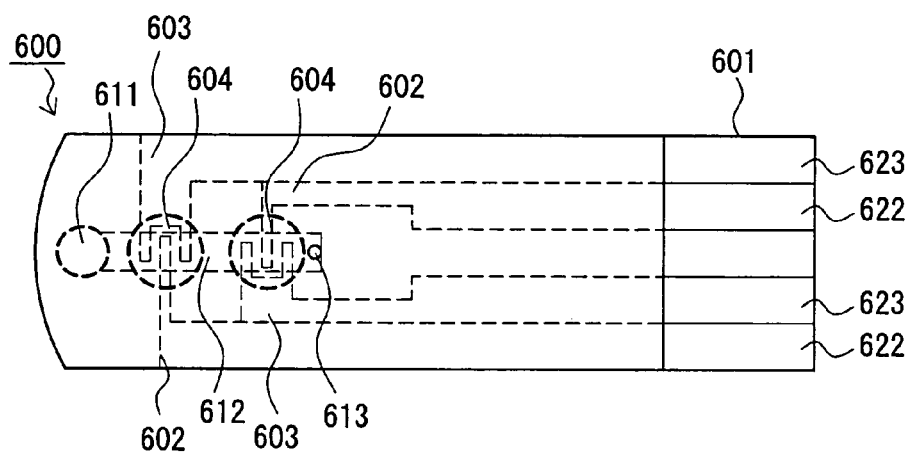
FIG. 6 is a plan view showing still another example of a sensor for blood component analysis according to the present invention.

Next, FIG. 6 shows an example of a sensor in which two analysis portions are provided in series. In this sensor 600, a lancing portion 611 is provided in one end portion of the sensor 600, and two analysis portions are provided in series toward the center of the sensor 600. These two analysis portions communicate with each other via a channel 612, and the channel 612 communicates with a through hole of the lancing portion 611. Thus, at the time of lancing, blood is guided by a burr formed when a needle or the like of a lancet breaks through a cover so that it is led to the channel 612 and then to the two analysis portions sequentially. Except for the above, the sensor 600 is configured in the same manner as the above sensor (see FIG. 1 and FIG. 2), and the size, materials, production method, method of use, etc. also are the same as those of the above sensor. In FIG. 6, reference numeral 601 denotes an insulating substrate, 602 denotes a working electrode, 603 denotes a counter electrode, 604 denotes a reagent layer, 613 denotes an air vent hole of the cover, and 622 and 623 denote a lead.

Figure 7:
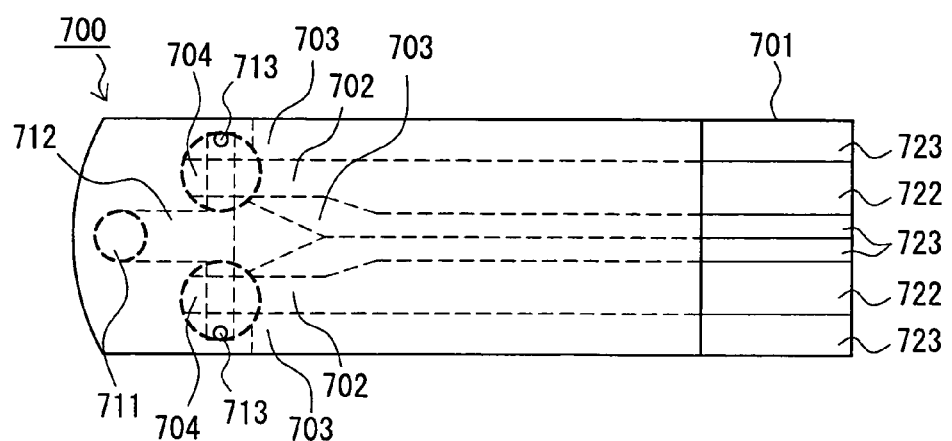
FIG. 7 is a plan view showing still another example of a sensor for blood component analysis according to the present invention.

Next, FIG. 7 shows an example of a sensor in which two analysis portions are provided in parallel. In this sensor 700, a lancing portion 711 is provided in one end portion of the sensor 700, and a channel 712 extends from the lancing portion 711 toward the center of the sensor 700 and then branches so that the channel 712 as a whole forms a T-shape. The analysis portions are provided on the ends of the branched portions, respectively. The channel 712 communicates with a through hole of the lancing portion 711. Thus, at the time of lancing, blood is guided by a burr formed when a needle or the like of a lancet breaks through a cover so that it is led to the channel 712 and then to the two analysis portions substantially simultaneously. Except for the above, the sensor 700 is configured in the same manner as the above sensor (see FIG. 1 and FIG. 2), and the size, materials, production method, method of use, etc. also are the same as those of the above sensor. In FIG. 7, reference numeral 701 denotes an insulating substrate, 702 denotes a working electrode, 703 denotes a counter electrode, 704 denotes a reagent layer, 713 denotes an air vent hole of the cover, and 722 and 723 denote a lead. Note here that in this example, instead of providing the air vent hole 713 in the cover, the T-shaped channel 712 may be formed so that the branched portions extend to side faces of the sensor and the tips thereof are open to the outside, thereby allowing these openings serve as air vent holes.

Figure 8:
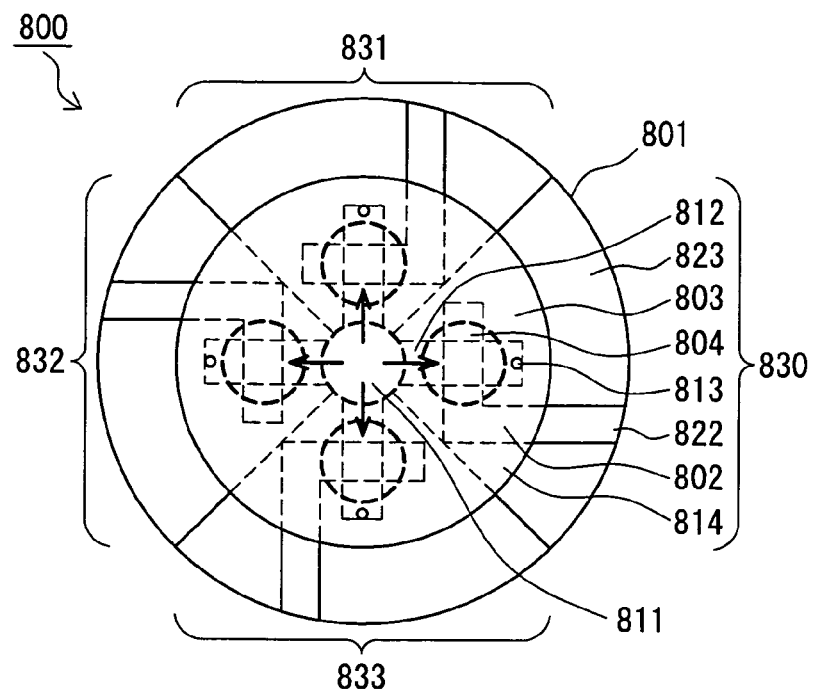
FIG. 8 is a plan view showing still another example of a sensor for blood component analysis according to the present invention.

Next, FIG. 8 shows an example of a sensor in which four analysis portions are provided radially with respect to one lancing portion. As shown in FIG. 8, in this sensor 800, a cover 814 is disposed on a circular insulating substrate 801 with a spacer (not shown) intervening therebetween. The sensor 800 is divided in the circumferential direction so as to give four equal portions, namely, a first region 830, a second region 831, a third region 832, and a fourth region 833. At the center of the sensor 800, one lancing portion 811 is provided. For example, in the first region 830, a channel 812 extends from a through hole of the lancing portion 811 toward an analysis portion. In the analysis portion, a reagent layer 804, a working electrode 802, and a counter electrode 803 are disposed. The same applies to the other regions. In the respective regions, the electrodes and leads as a whole have a shape of a sector. In the first region 830, the working electrode 802 and its lead 822 as a whole form a L-shape, and the counter electrode 803 and its lead 823 constitute the remaining portion. The same applies to the other regions. The cover 814 is in a circular shape that is smaller than the insulating substrate 801 so that the analysis portions are covered with the cover 814 but the leads are allowed to be exposed. The cover 814 has air vent holes provided so as to correspond to the four channels (an air vent hole 813 in the first region 830). Note here that the number of the analysis portions is not particularly limited in the present invention. Instead of providing four analysis portions as described above, two, three, or five or more analysis portions may be provided, for example. Moreover, the shape of the working electrode and its lead is not particularly limited, and thus is not limited to the above-described L-shape.

The size of the sensor 800 is not particularly limited. For example, the sensor 800 may have a diameter of 10 mm to 200 mm and a thickness of 0.1 mm to 5 mm, preferably a diameter of 20 mm to 150 mm and a thickness of 0.2 mm to 3 mm, and more preferably a diameter of 30 mm to 120 mm and a thickness of 0.2 mm to 1 mm. This sensor can be produced by laminating an insulating substrate, a spacer, and a cover that are formed in a predetermined shape and integrating them. In this sensor, other conditions such as materials are the same as those of the above sensor (see FIG. 1 and FIG. 2).

When the sensor 800 is placed on a pulp of a finger and a needle or the like of a lancet breaks through the lancing portion of the cover to injure the finger to cause bleeding, the blood is guided by a burr formed at this time so that, as indicated by the arrow, it is led to the respective channels and flows through the channels to be led to the respective analysis portions.

Figure 9:
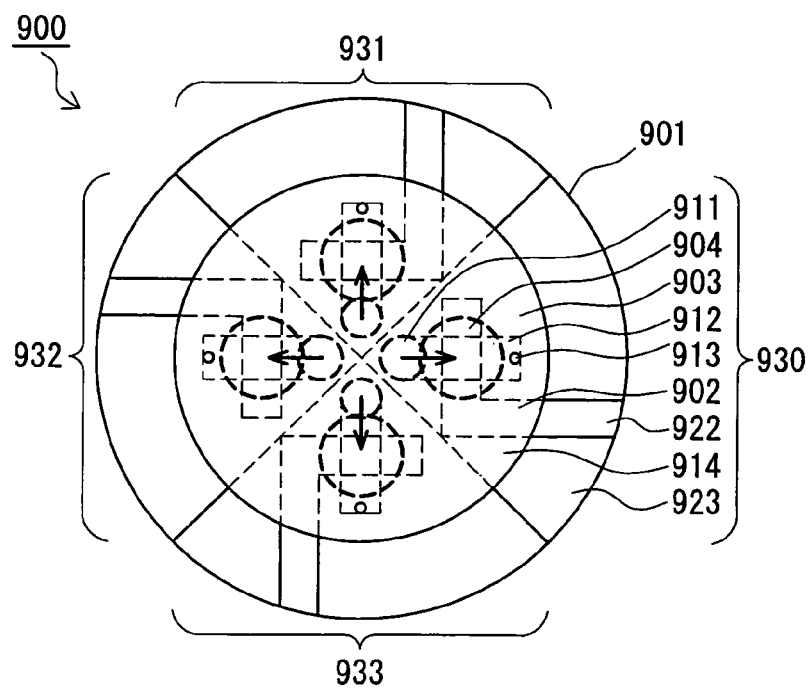
FIG. 9 is a plan view showing still another example of a sensor for blood component analysis according to the present invention.
Figure 10:
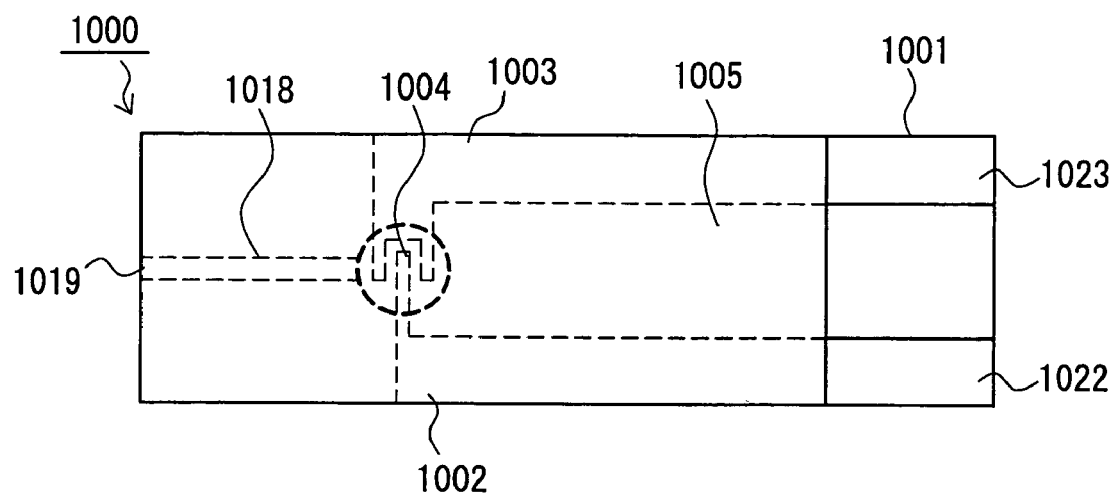
FIG. 10 is a plan view showing an example of a conventional sensor for blood component analysis.

Next, FIG. 9 shows an example of a cartridge-type sensor in which a plurality of sensor portions are formed on one substrate. As shown in FIG. 9, in this sensor 900, on a circular insulating substrate 901, a circular cover 914 that is smaller than the insulating substrate is disposed with a spacer (not shown) intervening therebetween. A sensor 900 is divided in the circumferential direction so as to give four equal portions, namely, a first sensor portion 930, a second sensor portion 931, a third sensor portion 932, and a fourth sensor portion 933. Each of the sensor portions has a shape of a sector. The sensor 900 has four lancing portions provided in one-to-one correspondence with the sensor portions at its center. For example, in the first sensor portion 930, a channel 912 extends from a through hole of a lancing portion 911 to an analysis portion, and a reagent layer 904, a working electrode 902, and a counter electrode 903 are disposed in the analysis portion. The same applies to the other sensor portions. In each of the sensor portions, the electrodes and leads as a whole have a shape of a sector. In the first sensor portion 930, the working electrode 902 and its lead 922 as a whole form a L-shape, and the counter electrode 903 and its lead 923 constitute the remaining portion. The same applies to the other sensor portions. The cover 914 is in a circular shape that is smaller than the insulating substrate 901 so that the analysis portions of the respective sensor portions are covered with the cover 914 but the leads are allowed to be exposed. The cover 914 has air vent holes provided so as to correspond to the four channels (an air vent hole 913 in the sensor portion 930). Note here that the number of the analysis portions is not particularly limited in the present invention. Instead of providing four analysis portions as described above, two, three, or five or more analysis portions may be provided, for example. Moreover, the shape of the working electrode and its lead is not particularly limited, and thus is not limited to the above-described L-shape. Also, the positions of the lancing portions are not particularly limited, and thus are not limited to the center of the circle as in the above. For example, the lancing portions may be provided closer to the circumference than the analysis portions so that blood flows from the circumferential side to the center of the circle.

The size of the sensor 900 is not particularly limited. For example, the sensor 900 may have a diameter of 10 mm to 200 mm and a thickness of 0.1 mm to 5 mm; preferably a diameter of 20 mm to 150 mm and a thickness of 0.2 mm to 3 mm; and more preferably a diameter of 30 mm to 120 mm and a thickness of 0.2 mm to 1 mm. This sensor can be produced by laminating an insulating substrate, a spacer, and a cover that are formed in a predetermined shape and integrating them. In this sensor, other conditions such as materials are the same as those of the above sensor (see FIG. 1 and FIG. 2).

This sensor 900 can be used as a cartridge type sensor. For example, the sensor 900 is set in a dedicated measuring device, and at first, the first sensor portion 930 is used. More specifically, the first sensor portion 930 is placed on a pulp of a finger, and a needle or the like of a lancet breaks through the lancing portion of the cover to injure the finger to cause bleeding. By so doing, the blood is guided by a burr formed at this time so that, as indicated by the arrow, it is led to the channel 912 and flows through the channel to be led to the analysis portion. After the completion of the measurement using the first sensor portion 930, subsequent measurement can be carried out by switching the selected sensor portion from the first sensor portion 930 to the second sensor portion 931 by rotation or the like, and performing lancing and blood supply to the analysis portion in the same manner as in the above. Measurement to be performed subsequent to this measurement also can be carried out by switching the selected sensor portion and performing the same operations.

As specifically described above, the present invention provides a sensor for blood component analysis, which allows even a trace amount of blood to be led to an analysis portion reliably. Thus, there is no particular limitation on the use of the sensor of the present invention as long as it is used for blood component analysis. For example, the sensor of the present invention is applicable to a clinical test, self-measurement of blood glucose level by diabetics, etc. Moreover, an analyte is not limited to glucose. For example, lactic acid, cholesterol, etc. can be an analyte of this sensor.

Specific embodiments and examples described in the detailed description of the present invention are intended merely to clarify the technical details of the present invention. The present invention should not be limited to such specific examples to be understood narrowly. The present invention can be changed variously to be carried out within the spirit of the present invention and the range of the following claims.

What is claimed is:

1. A collector and sensor for blood component analysis comprising:
   a substrate having a through hole;
   a spacer having a through hole;
   a cover; and
   a reagent layer,
   the cover being disposed on the substrate with the spacer intervening between the cover and the substrate, whereby
   a space between the substrate and the cover that communicates with the through hole of the spacer forms an analysis portion and a channel for leading a blood sample to the analysis portion inside the collector and sensor, with the reagent layer being disposed in the analysis portion, and
   the cover being breakable by a needle or a lancet, whereby a downwardly protruding burr of the broken cover forms a path for the blood sample from a blood collection part to the channel to the analysis portion,
   the through holes in the substrate and the spacer forming a common through hole through which the needle or an edge of the lancet and the burr of the broken cover can pass to the blood collection part when the spacer is disposed on the substrate that is placed over the blood collection part,
   the through hole of the spacer communicating with the channel and a top of the through hole of the spacer being covered with the cover, whereby
   a lancing portion is formed by the common through hole and a portion of the cover covering the top of the through hole of the spacer,
   wherein the portion of the cover forming a part of the lancing portion is hydrophilic, and
   wherein in use, the collector and sensor is placed at a position where blood collection is to be performed, the portion of the cover covering the lancing portion is broken through with the needle or the edge of the lancet so that the needle or the edge is allowed to pass through the common through hole to puncture the position, and the blood sample that has come out is guided by the burr formed when the cover is broken through so that the blood sample is led to the channel and flows through the channel to be led to the analysis portion.

2. The collector and sensor for blood component analysis according to claim 1, wherein a plurality of the channels and the analysis portions are provided with respect to one lancing portion.

3. The collector and sensor for blood component analysis according to claim 1, wherein a plurality of the lancing portions, the analysis portions, and the channels are present, and for each lancing portion, at least one channel and at least one analysis portion are formed.

4. The collector and sensor for blood component analysis according to claim 1, wherein an air vent hole is provided in a portion of the cover that corresponds to the channel.

5. The collector and sensor for blood component analysis according to claim 1, wherein the reagent layer is disposed on the substrate, a reagent in the reagent layer contains at least an oxidoreductase that reacts with an analyte, and an amount of the analyte is measured by causing a redox reaction between the oxidoreductase and the analyte contained in the blood sample and then measuring a degree to which the redox reaction has occurred.

6. The collector and sensor for blood component analysis according to claim 5, further comprising electrodes, wherein the electrodes are disposed in the analysis portion on the substrate so that a current generated by the redox reaction is measured by the electrodes.

7. The collector and sensor for blood component analysis according to claim 5, wherein the analyte is glucose in the blood sample, and the oxidoreductase is at least one of glucose oxidase and glucose dehydrogenase.

8. The collector and sensor for blood component analysis according to claim 5, wherein the reagent further comprises a mediator.

9. The collector and sensor for blood component analysis according to claim 1, wherein the spacer and the cover are separate components that are laminated with the substrate.

* * * * *